(12) United States Patent
Suzuki et al.

(10) Patent No.: US 10,981,913 B2
(45) Date of Patent: Apr. 20, 2021

(54) 11C-LABELED O6-BENZYLGUANINE, PET PROBE CAPABLE OF VISUALIZING O6-METHYL GUANINE METHYL-TRANSFERASE ACTIVITY, AND PRODUCTION METHOD OF THE SAME

(71) Applicant: NATIONAL CENTER FOR GERIATRICS AND GERONTOLOGY, Obu (JP)

(72) Inventors: Masaaki Suzuki, Obu (JP); Kengo Ito, Obu (JP); Atsushi Natsume, Obu (JP); Hiroshi Ikenuma, Obu (JP); Hiroko Koyama, Gifu (JP)

(73) Assignee: NATIONAL CENTER FOR GERIATRICS AND GERONTOLOGY, Obu (JP)

( * ) Notice: Subject to any disclaimer, the term of this patent is extended or adjusted under 35 U.S.C. 154(b) by 0 days.

(21) Appl. No.: 16/315,437

(22) PCT Filed: Jun. 3, 2017

(86) PCT No.: PCT/JP2017/020728
§ 371 (c)(1),
(2) Date: Jan. 4, 2019

(87) PCT Pub. No.: WO2018/008311
PCT Pub. Date: Jan. 11, 2018

(65) Prior Publication Data
US 2019/0308974 A1    Oct. 10, 2019

(30) Foreign Application Priority Data
Jul. 6, 2016    (JP) .............................. JP2016-134187

(51) Int. Cl.
*C07D 473/18* (2006.01)
*A61K 51/04* (2006.01)
*C07B 59/00* (2006.01)
*C07B 61/00* (2006.01)
*A61K 51/00* (2006.01)

(52) U.S. Cl.
CPC ............ *C07D 473/18* (2013.01); *A61K 51/00* (2013.01); *A61K 51/0453* (2013.01); *C07B 59/00* (2013.01); *C07B 61/00* (2013.01)

(58) Field of Classification Search
CPC .. C07D 473/18; A61K 51/00; A61K 51/0453; C07B 59/00; C07B 61/00
See application file for complete search history.

(56) References Cited

U.S. PATENT DOCUMENTS

2011/0263849 A1    10/2011    Suzuki et al.

FOREIGN PATENT DOCUMENTS

WO    WO 2010/074272 A1    7/2010

OTHER PUBLICATIONS

International Search Report (PCT/ISA/210) issued in PCT/JP2017/020728, dated Aug. 15, 2017.
(Continued)

*Primary Examiner* — Robert S Cabral
(74) *Attorney, Agent, or Firm* — Birch, Stewart, Kolasch & Birch, LLP (57) ABSTRACT

An object of the invention is to provide a $^{11}$C-labeled O$^6$-benzylguanine capable of obtaining a PET image and a process for producing the same.
The $^{11}$C-labeled O$^6$-benzylguanine of the invention is represented by the following chemical formula (a).

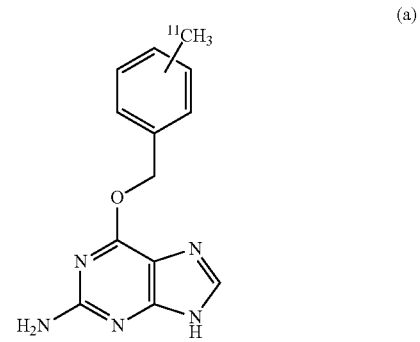

The $^{11}$C-labeled O$^6$-benzylguanine is produced by: a coupling step of cross-coupling a methyl iodide labeled with $^{11}$C and the following organotin compound (b) ($R^1$ represents an alkyl group, and $R^2$ and $R^3$ represent a leaving group which can be eliminated with a base) in the presence of a palladium complex, a phosphine ligand, and cuprous halide in an aprotic lactam; and a desorption step of desorbing the leaving groups $R^2$ and $R^3$ of the coupling product obtained by the coupling step with a base.

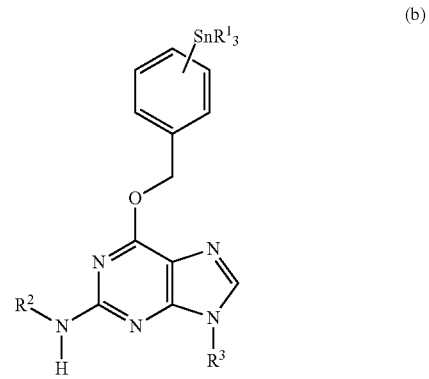

9 Claims, 5 Drawing Sheets

(56) References Cited

OTHER PUBLICATIONS

Keppler et al., "A general method for the covalent labeling of fusion proteins with small molecules in vivo", nature biotechnology, Jan. 2003, vol. 21, pp. 86-89.
Koyama et al., "Synthesis of PET probe $O^6$-[(3-[$^{11}$C]-methyl)benzyl]guanine by $Pd^0$-mediated rapid C-[$^{11}$C]methylation toward imaging DNA repair protein $O^6$-methylguanine-DNA methyltransferase in glioblastoma", Bioorganic & Medicinal Chemistry Letters, Mar. 18, 2017, vol. 27, No. 9, pp. 1892-1896.
Liu et al., "Synthesis and Preliminary Biological Evaluation of 6-O-[$^{11}$C]-[(methoxymethyl)benzyl]guanines, New Potential PET Breast Cancer Imaging Agents for the DNA Repair Protein AGT". Bioorganic & Medicinal Chemistry Letters, 2003, vol. 13, pp. 641-644.
Natsume et al., "A combination of IFN-β and temozolomide in human glioma xenograft models: implication of p53-mediated MGMT downregulation", Cancer Chemother Pharmacol, 2008, vol. 61, pp. 653-659.
Natsume et al., "IFN-β Down-Regulates the Expression of DNA Repair Gene MGMT and Sensitizes Resistant Glioma Cells to Temozolomide", Cancer Res 2005, vol. 65, pp. 7573-7579.
Pauly et al., "Substitution of Aminomethyl at the Meta-Position Enhances the inactivation of $O^6$-Alkylguanine-DNA Alkyltransferase by $O^6$-Benzylguanine", Journal of Medicinal Chemistry, 2008, vol. 51, No. 22, pp. 7144-7153.
Suzuki et al., ", Efficient synthesis of [11C]H-1152, a PET probe specific for Rho-kinases, highly potential targets in diagnostic medicine and drug development", Tetrahedron, 2012, vol. 68, No. 10, pp. 2336-2341.
Vaidyanathan et al., "Radiolabeled Guanine Derivatives for the in Vivo Mapping of $O^6$-Alkylguanine-DNA Alkyltransferase: 6-{4-[$^{18}$F] Fluoro-benzyloxy)•9H-purin-2-ylamine and 6-(3-[$^{131}$I]Iodo-benzyloxy )-9H-purin-2-ylamine", Bioconjugate Chem. 2000, vol. 11, pp. 868-875.
Wang et al., "Synthesis and preliminary biological evaluation of $O^6$-[4-(2-[$^{18}$F]fluoroethoxymethyl)benzyl]guanine as a novel potential PET probe for the DNA repair protein $O^6$-alkylguanine-DNA alkyltransferase in cancer chemotherapy", Bioorganic & Medicinal Chemistry, 2005, vol. 13, pp. 5779-5786.
Written Opinion (PCT/ISA/237) issued in PCT/JP2017/020728, dated Aug. 15, 2017.

HPLC observation of the change of the drug concentrations in blood within two hours after SD rat i.v. administration of pMeBG (3) (10 mg/kg).

[Fig. 8]

The plots of the mean plasma concentration-time profiles of mMeBG (2) and metabolites in rats by i.v. injection of 2 (10 mg/kg) under nonanesthesia ($n = 3$) and anesthesia ($n = 5$).
The concentrations were determined by an HPLC analytical method.

(conditions: mobile phase, methanol/$H_2O$ = 28:72; column, COSMOSIL® 5C18-MS-II 4.6 (i.d.) × 150 mm; flow rate, 1.5 mL/min; UV detection, 280 nm; column temperature, 30 °C).

[Fig. 9]

11C-LABELED 06-BENZYLGUANINE, PET PROBE CAPABLE OF VISUALIZING 06-METHYL GUANINE METHYL-TRANSFERASE ACTIVITY, AND PRODUCTION METHOD OF THE SAME

TECHNICAL FIELD

The present invention relates to a $^{11}$C-labeled $O^6$-benzylguanine, a PET probe capable of visualizing $O^6$-Methyl Guanine Methyl-Transferase activity, and a production method of the same.

BACKGROUND ART

In recent years, along with the progress of molecular biology, epigenetic research in genes has progressed, and the mechanisms of various diseases caused by dysregulation in gene transcription and translation have been elucidated.

Transcription of a gene encoding $O^6$-methylguanine-DNA-transferase (MGMT), a DNA repair enzyme in the brain, has been found to be regulated by methylation of its promoter site. In malignant brain tumors, Temodar has been developed as an anticancer agent that inhibits this regulatory function. Temodar generates methyldiazonium ions in vivo by the following reaction mechanism, and this methyldiazonium ion methylates DNA including the promoter site of MGMT, thereby functioning as an anticancer agent (see the following reaction formula).

However, when Temodar is prescribed as a remedy for malignant brain tumor overexpressing MGMT which is a demethylase, it may show drug resistance (reaction to the left side in the lower reaction of formula above) and it hindered the treatment. It has also been clarified that the difference in sensitivity/insensitivity of brain tumor cells to Temodar is due to the expression level of MGMT (Non-Patent Document 1 and Non-Patent Document 2). Therefore, in the treatment method using Temodar in malignant brain tumor as an anticancer agent, it is indispensable to quantify MGMT in the tumor by biopsy.

However, in order to quantify MGMT in the tumor, there is no other means other than to excise the tumor out of the body by surgical operation and quantify the expression level of MGMT by a biochemical method. The surgical operation was a heavy burden on the patient.

In order to solve this problem, attempts have been made to PET probe $O^6$-benzylamine, an MGMT inhibitor (Non-Patent Document 3 and Non-Patent Document 4). The principle is as follows.

That is, it is known that $O^6$-benzylguanine irreversibly benzylates a thiol at a cysteine site for performing a demethylation reaction by MGMT, thereby inhibiting the demethylation reaction (Non-Patent Document 5). Therefore, if the benzyl group of $O^6$-benzylguanine is labeled, it is considered that the labeled benzyl group irreversibly binds to MGMT and can be imaged with a PET apparatus. Based on these principles, $O^6$-benzylguanine in which the benzene

[Formula 1]

ring has been labeled by [$^{18}$F] fluorination has been synthesized (Non-Patent Document 3, Non-Patent Document 4), and O$^6$-benzylguanine in which the benzene ring is labeled with [$^{11}$C] methoxy group has been synthesized (Non-Patent Document 4). However, the $^{18}$F labeled compound is synthesized via a complicated process consisted by multiple stages even after labeling, and the $^{11}$C labeling method lacks the reaction selectivity of the labeled site, and the obtained $^{11}$C labeled body is metabolically unstable in vivo. In addition, there have been no reports of PET images regarding to MGMT of these labeled probes.

PRIOR ART DOCUMENTS

Patent Document

Patent Document 1: WO2010-074272A

Non-Patent Documents

Non-Patent Document 1: A. Natsume, D. Ishii, T. Wakabayasi, T. Tsuno, H. Hatano, M. Mizuno, J. Yashida, Cancer Res. 2005, 65, 7573-7579.
Non-Patent Document 2: A. Natsume, T. Wakabayashi, D. Ishii H. Maruta, M. Fujii, S. Shimoto, M. Ito, J. Yoshida, Cancer Chemother. Pharmacol. 2008, 61, 653-659.
Non-Patent Document 3: G. Vaidyanathan, D. J. Affleck, C. M. Cavazos. S. P. Johnson, S. Shankar, H. S. Friedman, M. O. Colvin, M. R. Zalutsky, *Bioconjugate Chem.* 2000, 11, 868-875.
Non-Patent Document 4: X. Liu, Q.-H. Zheng, X, Fei, J.-Q. Wang, D. W. Ohannesian, L. C. Erickson, K. L. Stone, G. D. Hutchins, *Bioorg. Med. Chem. Lett.* 2003, 13, 641-644.
Non-Patent Document 5: A. Keppler, S. Gendreizing, T. Gronemeyer, H. Pick, H. Vogel, K. Johnsson, Nature Biol. 2003, 21, 86-89.

SUMMARY OF THE INVENTION

Problems to be Solved by the Invention

The present invention has been made in view of the above conventional problems. The present invention can be said to be the ideal type of radioactive compound synthesis method. The present invention is a high-efficiency synthesis method in which a labeling reaction is incorporated into the final step of synthesis by a one-pot operation. The present invention provides $^{11}$C-labeled O$^6$-benzylguanine having sufficient radioactivity for PET imaging, a method for producing the same, and a PET probe containing $^{11}$C-labeled O$^6$-benzylguanine.

Means for Solving the Problems

In order to solve the above problem, the present inventor has planned labeling of benzyl group of O$^6$-benzylguanine with [$^{11}$C] CH$_3$. Since the $^{11}$C-labeled position by the carbon-[$^{11}$C] carbon bond is metabolically very stable, it is considered that a highly reliable PET image can be obtained. In addition, since the methyl group is the smallest nonpolar substituent, it can be expected that the inhibitory effect of O$^6$-benzylguanine on MGMT is not significantly affected by [$^{11}$C] methylation.

However, since half-life of $^{11}$C is as short as 20 minutes, it must be separated and purified rapidly after the reaction, administered to the living body, and measured with a PET apparatus. Therefore, the present inventors tried to apply the coupling reaction (Patent Document 1) of a radionuclide-containing iodinated [$^{11}$C] methyl and a tin compound having a heteroaromatic ring developed.

However, even if the method of Patent Document 1 is carried out as it is, $^{11}$C-labeled O$^6$-benzylguanine having sufficient radioactivity could not be obtained to obtain a PET image, because unprotected O$^6$-benzylguanine has an amino group which inhibits the reaction via palladium in the molecule. For this reason, as a result of more intensive research, we successfully synthesized $^{11}$C-labeled O$^6$-benzylguanine capable of solving this problem, and we have completed the present invention.

That is, the $^{11}$C-labeled O$^6$-benzylguanine of the present invention is characterized by being represented by the following chemical formula (a).

[Formula 2]

The present inventors have synthesized the compound of the above chemical formula (a) and have confirmed from the measurement of its radioactivity that PET probes are sufficiently usable. So, MGMT imaging becomes possible by imaging PET images by administering PET probes containing the compound of the above chemical formula (a) administered to a living body. This is because this PET probe binds irreversibly to MGMT.

The method for producing the $^{11}$C-labeled O$^6$-benzylguanine of the present invention comprises:

a coupling step of cross-coupling a methyl iodide labeled with $^{11}$C and the following organotin compound (b) (R1 represents an alkyl group, and R$^2$ and R$^3$ represent a leaving group which can be eliminated with a base) in the presence of a palladium complex, a phosphine ligand, and cuprous halide in the aprotic lactam, and a desorption step of desorbing the leaving groups R$^2$ and R$^3$ of the coupling product obtained by the coupling step with a base.

[Formula 3]

In the coupling step of this production method, the phosphine ligand is sterically coordinated to the palladium complex in an unsaturated manner to create an active reaction field. Methyl iodide labeled with $^{11}C$ is oxidatively added to the palladium complex to which the phosphine ligand is coordinated, whereby a palladium complex in which the phosphine ligand is coordinated to $[^{11}C]$ $CH_3PdI$ is formed.

On the other hand, the organotin compound (b) becomes an organic copper compound rich in nucleophilicity through a metal exchange reaction with cuprous halide.

Then, the palladium complex in which the phosphine ligand is coordinated to $[^{11}C]$ $CH_3PdI$ and the organic copper compound undergo a substitution reaction, further the reductive elimination takes place, and the coupling reaction of $[^{11}C]$ $CH_3$ is completed.

$R^2$ and $R^3$ are eliminated by a base in the desorption step, and the target $^{11}C$-labeled $O^6$-benzylguanine (a) is produced.

The substituents $R^2$ and $R^3$ are not particularly limited as long as they are leaving groups which can be eliminated with a base. For example, $R^2$ includes a trifluoroacetyl group, a tert-butoxycarbonyl group, a trityl group and the like, and particularly preferred is a trifluoroacetyl group. For example, $R^3$ include a tert-butoxycarbonyl group, a trifluoroacetyl group, a benzyloxycarbonyl group, a trityl group and the like, and a tert-butoxycarbonyl group is particularly preferable.

As a solvent in the coupling step, an aprotic lactam is used. the aprotic lactam refers to a cyclic amide (ie, a lactam) which does not have a hydrogen directly bonded to nitrogen. The preferred aprotic lactam is N-alkyl-2-pyrrolidinone, and the alkyl group preferably has 1 to 6 carbon atoms, more preferably 1 to 3 carbon atoms.

It is also preferable to add at least one of a carbonate salt, a fluoride of an alkali metal, and an alkali metal salt of ascorbic acid in the coupling step. In this case, trialkyltin halide produced as a by-product in the coupling step reacts with at least one of a carbonate, a fluoride of an alkali metal, and an alkali metal salt of ascorbic acid and is excluded from the reaction system by neutralization or precipitation (in the case of carbonate, it precipitates as trialkylstannyl carbonate, in the case of alkali metal fluoride, it precipitates as trialkylstannyl fluoride, in the case of the alkali metal salt of ascorbic acid, it precipitates as ascorbic acid). Therefore, the metal exchange reaction from Sn to Cu is promoted, and the yield can also be increased.

Advantageous Effects of Invention

The $^{11}C$-labeled $O^6$-benzylguanine obtained by the production method of the present invention has sufficient radioactivity to obtain a PET image and can be used as a PET probe. In the $^{11}C$-labeled $O^6$-benzylguanine of the present invention, the $^{11}C$-labeled benzyl moiety is irreversibly bonded to MGMT and the MGMT concentration is quantified from the radioactivity concentration (SUV value corrected by dose and body weight) of the target site obtained from PET imaging. Further, in the method for producing $^{11}C$-labeled $O^6$-benzylguanine of the present invention, since the $^{11}C$-labeled position is metabolically stable, a PET probe having high reproducibility and high quality is provided. In addition, since the deprotection step after the coupling step proceeds quickly and easily, it is possible to carry out label synthesis by using a general radiopharmaceutical automatic synthesizer.

On the contrary, in Non-Patent Document 3, $^{18}F$-labeled $O^6$-benzyl Guanine is synthesized by carrying out multistage synthesis of benzylation of 6-chloro-2-amino-9H-purine (or 2-amino-6-trimethylamino-9H-purine hydrochloride) with $[^{18}F]$ fluorobenzyl alcohol reduced from $^{18}F$-labeled benzaldehyde as a pro-setting group. Since this reaction involves a complicated operation, it is difficult to perform the reaction using a general automatic synthesizer.

In Non-Patent Document 4, $^{11}C$-labeled $O^6$-benzylguanine in which the benzene ring is labeled with $[^{11}C]$ methoxy group is synthesized by O-$[^{11}C]$ methylation reaction of $O^6$-(hydroxymethyl) benzylguanine with highly reactive $[^{11}C]$ methyl triflate. In this reaction, $[^{11}C]$ methylated form of the guanine moiety due to $[^{11}C]$ methylation (N-$[^{11}C]$ methylation) of a highly nucleophilic amine is by-produced, so the yield of the target label is low.

MODE FOR CARRYING OUT THE INVENTION

Study on Methylation of O⁶-benzylguanine

[Formula 4]

The introduction position of the [¹¹C] methyl group of the benzene ring present in the above-mentioned O⁶-benzylguanine (1) was investigated. For this purpose, unlabeled O⁶-(3-methylbenzyl) guanine (2), O⁶-(4-methylbenzyl) guanine (3) and O⁶-(3,5-dimethylbenzyl) guanine (4) were synthesized by reaction of corresponding alcohols with 2-amino-6-chloropurine according to the method described in the following literature of Liu et al. Then, the inhibitory activity of these MGMTs was investigated.

X. Liu, Q.-H. Zheng, G. D. Hutchins, X. Fei, L. C. Erickson, K. D. Miller, B. H. Mock, B. E. Glick-Wilsob, W. L. Winkel, K. L. Stone, K. A. Carlson, *Synth. Commun.* 2003, 33, 941-952.

Figure 1:
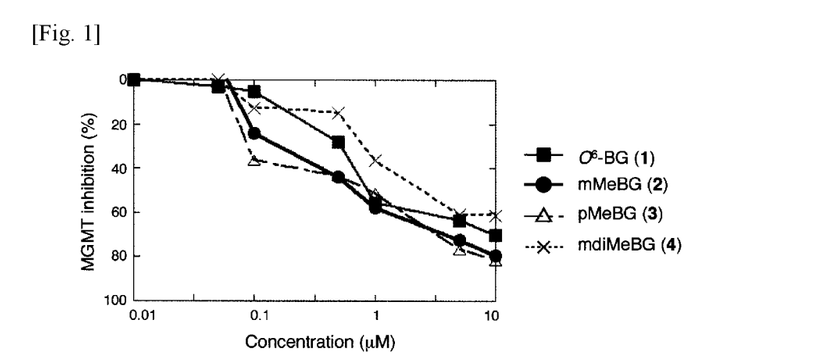
FIG. 1 is a graph showing the MGMT inhibitory effect of the compounds (1) to (4).

The enzyme inhibitory activity against MGMT of O⁶-(3-methylbenzyl) guanine (2), O⁶-(4-methylbenzyl) guanine (3) and O⁶-(3,5-dimethylbenzyl) guanine (4), were investigated using fluorescent quantitatively labeled oligonucleotide substrates with DNA damage specific to MGMT for quantification. As a result, these three compounds all had MGMT inhibitory effect similar to O⁶-benzylguanine (1), particularly O⁶-(3-methylbenzyl) guanine (2) and O⁶-(4-methylbenzyl) guanine 3) had a slightly higher inhibitory activity than O⁶-BG (1) (see FIG. 1). Based on this result, the inventors used O⁶-(3-methylbenzyl) guanine (2) as a target for labeling by ¹¹C.

Figure 2:
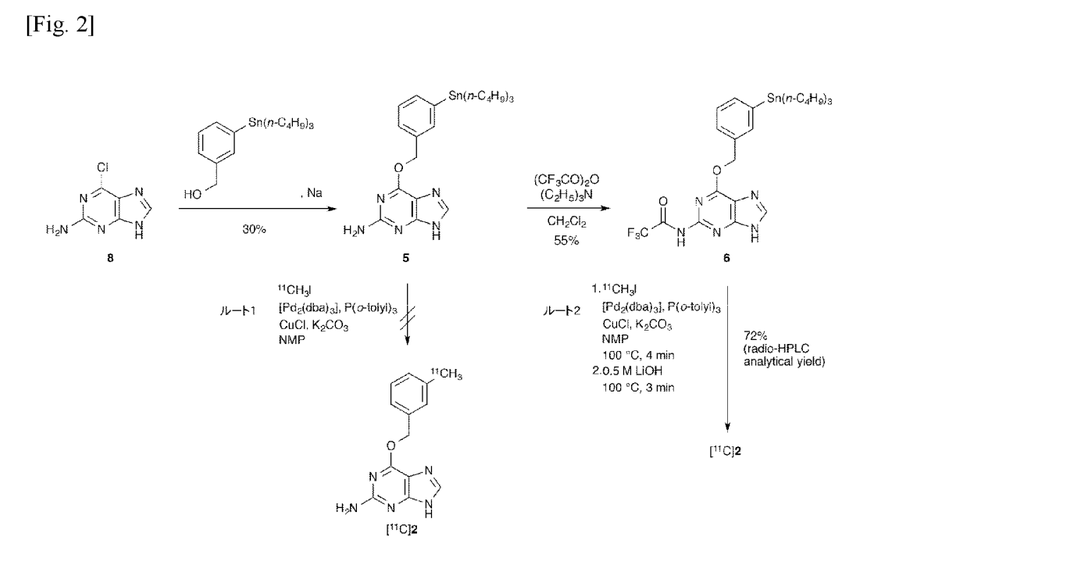
FIG. 2 is a diagram showing a synthetic route of methylation of organotin compound 5 having no protecting group for amino group and organotin compound 6 having amino group protected with trifluoro group by $[^{11}C]$ $CH_3I$.
Figure 3:
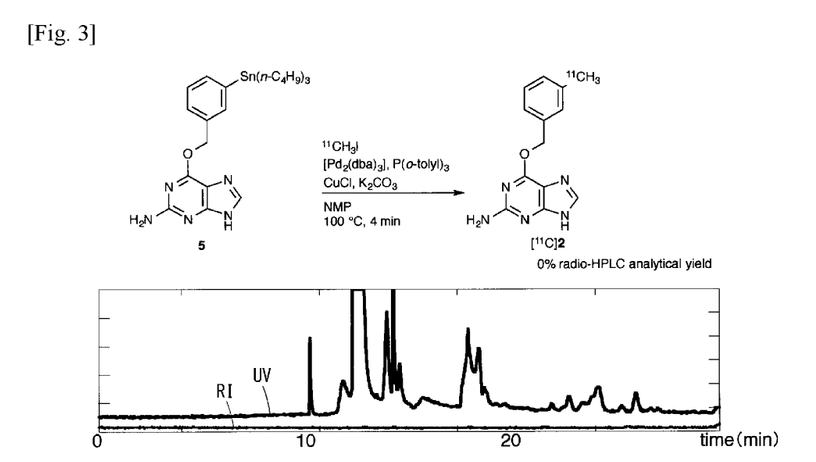
FIG. 3 is a labeling synthesis reaction formula and an HPLC chart in the case where the organotin compound 5 not protected with an amino group is methylated by $[^{11}C]$ $CH_3I$.
Figure 4:
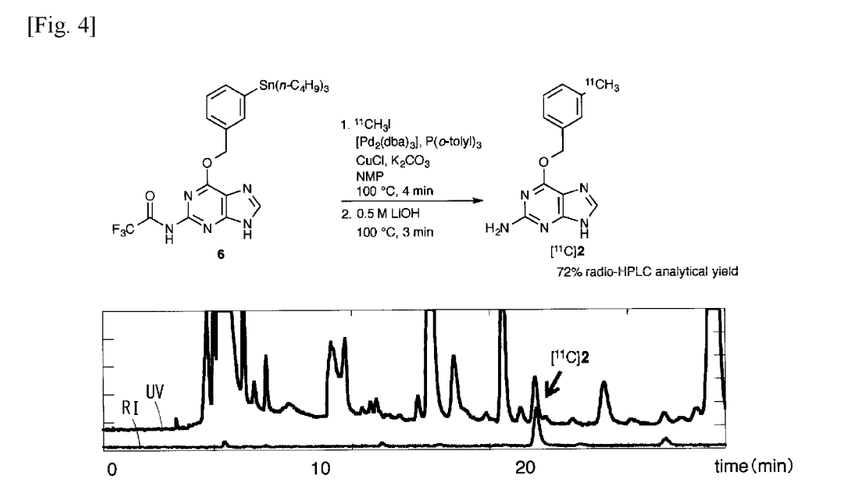
FIG. 4 is a labeling synthesis reaction formula and an HPLC chart in the case where the organotin compound 6 having the amino group at the 2-position protected with a trifluoroacetyl group is methylated by $[^{11}C]CH_3I$.

Specifically, we decided to utilize the sp³-sp² (heteroaromatic ring) type cross-coupling reaction between [¹¹C] CH₃I and the heteroaromatic ring organotin compound using the Pd⁰ catalyst we have already developed (Patent document 1). In consideration of the effect of using bulky phosphine ligand in excess on the Pd⁰ complex, the effect of using an aprotic polar solvent, and the effect of addition of copper ions and base to prevent progress of tinning reaction by acidic protons, the reaction was carried out under the condition of [Pd₂(dba)₃]/P(o-CH₃C₆H₄)₃/CuCl/K₂CO₃/NMP solvent. However, almost no desired ¹¹C-labeled O⁶-benzylguanine was obtained (see Route 1 in FIG. 2 and FIG. 3). Therefore, a two-step synthesis method was tried in which the amino group contained in the guanine structure was protected with trifluoroacetate with trifluoroacetic anhydride and deprotection reaction was carried out after the reaction. Then, introduction of the protecting group occurred only at the 2-amino group of O⁶-benzylguanine, and an organotin compound 6 was obtained. This compound was subjected to [¹¹C] CH₃ conversion under the same conditions and deprotected with lithium hydroxide, whereby O⁶-(3-methylbenzyl) guanine (2) labeled with ¹¹C was obtained with 72% HPLC analysis yield (See Route 2 in FIG. 2 and FIG. 4).

Figure 6:
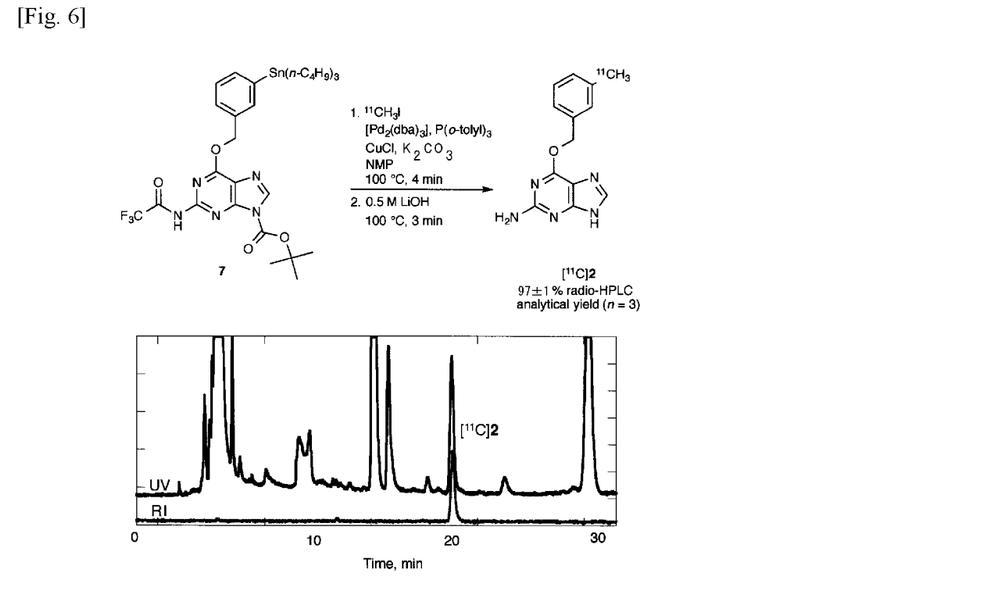
FIG. 6 is a labeling synthesis reaction formula and an HPLC chart in the case where an organotin compound 7 in which the amino group at the 2-position is protected with a trifluoroacetyl group and the amino group at the 9-position is protected with a tert-butoxycarbonyl (BOC) group is methylated by $[^{11}C]$ $CH_3I$ ($K_2CO_3$ is added as a base).

Furthermore, an organotin compound 7 in which the amino group at the 2-position of O⁶-benzylguanine was protected with a TFA group and the amino group at the 9-position was protected with a tert-butoxycarbonyl (BOC) group was prepared and deprotected with a strong base, O⁶-(3-methylbenzyl) guanine (2) labeled with the objective ¹¹C-labeled compound was obtained with high HPLC analysis yield of 97±1% (see FIG. 6). The total time for synthesis and purification in this case is 47 minutes, the total radiation is 1.34 GBq, the specific activity is 95-99 GBq/mmol, the disintegration-corrected yield is 19%, the chemical purity is 99% or more, the radiochemical purity is 99% or more, which was found to be sufficiently usable as a PET probe.

Hereinafter, embodiments of the present invention will be described in detail.

(Analyzer and Conditions Used in Examples)

¹H, ¹³C, ¹⁹F NMR was measured by ECS 400 manufactured by JEOL Ltd. The chemical shift was set to 0.00 ppm when TMS was used as a standard, this was set to 7.26 for ¹H NMR and 77.0 for ¹³C NMR when CHCl₃ was used as a standard, and was set at −76.55 ppm for ¹⁹F NMR with CF₃COOH as a standard. Also, the abbreviations s, d, t, q and m represent singlet, doublet, triplet, quartet, and multiplet, respectively. For high resolution mass spectrometry (HRMS), PE Biosystems, Mariner system or JEOL JMS-700/GI was used. All [¹¹C] methylation reactions were performed remotely in a draft shielded with lead. [$^{11}$C] CO$_2$ was produced by a $^{14}$N (p, α) $^{11}$C nuclear reaction using a CYPRIS HM-18 cyclotron (manufactured by Sumitomo Heavy Industries, Ltd.). Heating, dilution of the reaction mixture, injection of sample into HPLC, collection and concentration of fractions were carried out by a radiopharmaceutical automatic synthesizer to obtain $^{11}$C-labeled compound. Radioactivity was quantified with ATOMLAB™ 500 dose calibrator (Biodex Medical Systems, Inc.). The synthesized [$^{11}$C]methylated compound was analyzed by Shimadzu HPLC system combining bias supply 925-SCINT (AMETEK Co., Ltd.) and linear count rate meter 7131-1 (Ohyo Koken Kogyo Co., Ltd.). The Shimadzu HPLC system consists of system controller (SPD—10 Avp), online degasser (DGU—12 A), solvent delivery unit (LC—10 ATvp), column oven (CTO—10 A), photodiode array detector (SCL—10 Avp) and software (LC-solution).

Synthesis of O$^6$-[3-(tributylstannyl)benzyloxy]guanine (5)

3-(Tributylstannyl)benzyl alcohol (8.5 g, 21 mmol) was placed in a 30 mL round bottom flask and heated to 130° C. Then, under a nitrogen stream, sodium (197 mg, 8.6 mmol) was added. After confirming that all the sodium was dissolved, the temperature was lowered to 115° C. and 2-amino-6-chloropurine (8, 1.2 g, 7.1 mmol) was added under an argon stream. And the mixture was stirred at the same temperature overnight. The obtained solution was cooled to room temperature, the undissolved solid was removed by filtration, the filtrate was concentrated under reduced pressure, and the resulting material was subjected to silica gel column chromatography using a mixed solution of dichloromethane:methanol=9:1 as an eluent, 51.15 g (2.17 mmol, 30.4%) of the compound was obtained as a pale yellow solid.

$δ_H$ (400 MHz; CDCl$_3$) 0.86 (9H, t, J=7.4 Hz, CH$_3$), 0.95-1.11 (6H, m, CH$_2$), 1.26-1.35 (6H, m, CH$_2$), 1.48-1.56 (6H, m, CH$_2$), 5.02 (2H, s, NH$_2$), 5.54 (2H, s, CH$_2$), 7.28-7.64 (4H, m, Ph), 7.70 (1H, s, NCH), 11.4-12.3 (1H, brs, NH); $δ_C$ (100 MHz; CDCl$_3$) 9.6 (3C), 13.7 (3C), 27.4 (3C), 29.1 (3C), 68.7, 128.0, 128.3, 128.7, 135.5, 136.4, 136.5, 142.3, 159.2).

Synthesis of O$^6$-[3-(tributylstannyl)benzyloxy]-N$^2$-(trifluoroacetyl)guanine (6)

Triethylamine (53 μL, 37 mg, 0.38 mmol) was added to a solution (5 mL) of Compound 5 (192 mg, 0.363 mmol) in dry dichloromethane, and the mixture was cooled to 0° C. Trifluoroacetic anhydride (53 μL, 80 mg, 0.38 mmol) was added to the mixture and the mixture was stirred for 2 hours. The reaction mixture solution was poured into 10 ml of water and extracted three times with 10 ml of dichloromethane and then the organic layer was combined and washed with 15 ml of water and 15 ml of brine and dried with anhydrous sodium sulfate. After filtration, concentration was carried out. The obtained crude product was purified by column chromatography (silica gel (50 g), dichloromethane:methanol=20:1), Compound 6 (125 mg, 0.201 mmol, 55.3%) was obtained.

$δ_H$ (400 MHz; CDCl$_3$) 0.87 (9H, t, J=7.4 Hz, CH$_3$), 0.97-1.11 (6H, m, CH$_2$), 1.25-1.34 (6H, m, CH$_2$), 1.48-1.56 (6H, m, CH$_2$), 5.66 (2H, s, CH$_2$), 7.33-7.56 (4H, m, Ph), 8.33 (1H, s, NCH), 8.62 (1H, s, NHCOCF$_3$), 12.7 (1H, s, NH); $δ_C$ (100 MHz; CDCl$_3$) 9.5 (3C), 13.6 (3C), 27.3 (3C), 27.9 (3C), 29.0 (3C), 70.1, 87.6, 120.1, 128.0, 128.9, 134.5, 136.7, 137.0, 141.0, 142.5, 145.8, 151.3, 152.0, 153.5 (q, $^1$J($^{13}$C-$^{19}$F)=38.3 Hz), Ph 161.4, 153.171.1; $δ_F$ (MHz; CDCl$_3$) −76.80 (s, CF$_3$).

11
Synthesis of N-(tert-butoxycarbonyl)-O$^6$-(3-bromobenzyl)guanine (11)

[Formula 7]

12
Synthesis of N$^9$-(tert-butoxycarbonyl)-O$^6$-[3-(tributylstannyl)benzyl]guanine (12)

[Formula 8]

O$^6$-(3-Bromobenzyl) guanine (10, 1.41 g, 4.42 mmol) was added to a solution of potassium tert-butoxide (496 mg, 4.42 mmol) in ethanol (5 mL) at 0° C. under an argon stream. After 30 minutes, ethanol was removed under reduced pressure. The residue was dissolved in DMF (5 mL) and brought to 0 C, and a solution DMF (2 mL) of (Boc)$_2$O (978 μL, 964 mg, 4.42 mmol) was added. The mixture was stirred overnight at room temperature, quenched with water and extracted with ethyl acetate. The crude product was purified by column chromatography (silica gel (50 g), dichloromethane:methanol=20:1), Compound 11 (125 mg, 0.201 mmol, 55.3%) as a pale yellow solid was obtained.

$\delta_H$ (400 MHz; CDCl$_3$) 1.67 (9H, s, CH$_3$), 5.16 (2H, s, NH$_2$), 5.51 (2H, s, CH$_2$), 7.23 (1H, t, J=8.8 Hz, Ph), 7.41 (1H, d, J=8.8 Hz, Ph), 7.47 (1H, d, J=8.8 Hz, Ph), 7.64 (1H, s, Ph), 8.01 (1H, s, NCH); $\delta_C$ (100 MHz; CDCl$_3$) 28.0 (3C), 67.2, 86.3, 115.9, 122.5, 130.0, 131.2 (2C), 137.8, 138.4, 146.1, 153.9, 160.5, 161.0.

Compound 11 (576 mg, 1.36 mmol), hexabutyl distannane (2.0 mL, 2.4 g, 4.1 mmol), tetrakis (triphenylphosphine) palladium (0) (157 mg, 0.136 mmol) was added to a dried 50 ml Schlenk tube in an argon atmosphere, and freshly distilled 1,4-dioxane (10 mL) was added. The mixture was heated to 80° C., stirred overnight, then cooled to room temperature and a palladium component was removed by passing the reaction through celite. The filtrate was concentrated in vacuo and the residue was purified by silica gel column chromatography using an eluent of hexane:ethyl acetate=3:1, 629 mg (73% yield) of Compound 12 as a pale yellow solid was obtained.

$\delta_H$ (400 MHz; CDCl$_3$) 0.87 (9H, t, J=7.4 Hz, CH$_3$), 0.98-1.11 (6H, m, CH$_2$), 1.27-1.36 (6H, m, CH$_2$), 1.49-1.57 (6H, m, CH$_2$), 1.66 (9H, s, CH$_3$), 5.14 (2H, s, NH$_2$), 5.55 (2H, s, CH$_2$), 7.32 (1H, t, J=7.3 Hz, Ph), 7.41 (1H, d, J=7.3 Hz, Ph), 7.45 (1H, d, J=7.3 Hz, Ph), 7.54 (1H, s, Ph), 8.00 (1H, s, NCH); $\delta_C$ (100 MHz; CDCl$_3$) 9.6 (3C), 13.6 (3C), 27.3 (3C), 28.0 (3C), 29.0 (3C), 68.7, 86.2, 116.0, 127.9, 128.4, 135.3, 136.3, 136.6, 137.5, 142.2, 146.2, 153.8, 160.5, 161.4.

Synthesis of N⁹-(tert-butoxycarbonyl)-O6-[3-(tributylstannyl)benzyl]-N2-(trifluoroacetyl)guanine (7)

Trimethylamine (153 μL, 101 mg, 962 μmol) was added to a dry dichloromethane (5 mL) solution of Compound 12 (629 mg, 0.998 mmol), after cooling the mixed solution to 0° C., trifluoroacetic anhydride (153 μL, 231 mg, 1.10 mmol) was added and the mixture was stirred for 2 hours. The reaction solution was poured into about 10 ml of water and extracted with dichloromethane (15 ml×3). The organic layers were combined, washed with water (15 mL) and brine (15 mL), and then dried over anhydrous sodium sulfate. The crude product obtained by filtration and concentration of the solution was purified by column chromatography (silica gel (5 g), hexane/acetone=3:1), Compound 7 (330 mg, 0.454 mmol, 45.5%) as a colorless solid was obtained.

$\delta_H$ (400 MHz; CDCl$_3$) 0.87 (9H, t, J=7.4 Hz, CH$_3$), 0.98-1.11 (6H, m, CH$_2$), 1.26-1.34 (6H, m, CH$_2$), 1.48-1.54 (6H, m, CH$_2$), 1.71 (9H, s, CH$_3$), 5.69 (2H, s, CH$_2$), 7.33 (1H, t, J=7.3 Hz, Ph), 7.43 (1H, d, J=7.3 Hz, Ph), 7.53 (1H, d, J=7.3 Hz, Ph), 7.63 (1H, s, Ph), 8.31 (1H, s, NCH), 8.61 (1H, s, NH); $\delta_C$ (100 MHz; CDCl$_3$) 9.5 (3C), 13.6 (3C), 27.3 (3C), 27.9 (3C), 29.0 (3C), 70.1, 87.6, 120.1, 128.0, 128.9, 134.5, 136.7, 137.0, 141.0, 142.5, 145.8, 151.3, 152.0, 153.5 (q, $^1J(^{13}C-^{19}F)$=38.3 Hz), Ph 161.4, 153.171.1; $\delta_F$ (MHz; CDCl$_3$) −76.75 (s, CF$_3$).

HRMS (ESI) m/z:
[M+H]⁺ calcd for C$_{31}$H$_{45}$F$_3$N$_5$O$_4$ $^{120}$Sn 728.2446; found 728.2464

[M+Na]⁺ calcd for C$_{31}$H$_{45}$F$_3$N$_5$O$_4$ $^{120}$Sn 750.2265; found 750.2267

Synthesis of O⁶-(3-methylbenzyl)-guanine (2)

[Pd$_2$(dba)$_3$] (1.0 mg, 1.1 μmol), P(o-tolyl)$_3$ (5.4 mg, 18 μmol), CuCl (0.4 mg, 4 μmol), and K$_2$CO$_3$ (0.8 mg, 5 μmol) were added to a 1 mL Schlenk tube filled with dried argon gas. A NMP (300 μL) solution of organotin compound 7 (8.7 mg, 12 μmol) was introduced into a Schlenk tube cooled to −10° C. through a stainless steel cannula. Further, after adding a methyl iodide solution (12 μL, 0.10 M in DMF, 1.2 μmol), the mixture was reacted at 80° C. for 4 minutes. Then, a 1.0 M LiOH aqueous solution (600 μL) was added and after stirring at 80° C. for 3 minutes, the reaction solution was quickly cooled in an ice bath. The mixture obtained was introduced into a short column of silica gel (1 g), eluted with acetonitrile (2 mL), and a naphthalene solution (0.10 M DMF, 10 μL, 1.0 μmol) was added as an internal standard. The solution obtained was analyzed by HPLC (mobile phase, acetonitrile/20 mM sodium dihydrogenphosphate=40:60; column, CAPCELL PAK C18 MG 5 μm, 4.6 (id)×250 mm flow rate 1 mL/min UV detection 280 nm Retention time 3.4 min). As a result, the yield of Compound 2 was 100%. Identification of compound 2, using organotin compound 7 (8.7 mg, 12 μmol) and methyl iodide (120 μL, 0.10 M in DMF, 12 μmol) [Pd$_2$(dba)$_3$]/P(o-CH$_3$C$_6$H$_4$)$_3$/CuCl/K$_2$CO$_3$ (1:16:2:5 molar ratio) and reacted at 80° C., was carried out by ¹H NMR.

¹H NMR (DMSO-d$_6$) δ=2.32 (s, 3H, CH$_3$), 5.44 (s, 2H, CH$_2$), 6.26 (s, 2H, NH$_2$), 7.16-7.29 (m, 4H, Ar), 7.82 (s, 1H, guanine H8), 12.51 (broad s, 1H, guanine H9).

Synthesis of $O^6$-(3-[$^{11}$C]methylbenzyl)guanine ([$^{11}$C](2)) when $K_2CO_3$ is Used as a Base A mixture of [Pd$_2$(dba)$_3$] (1.0 mg, 1.1 μmol), P(o-tolyl)$_3$ (3.4 mg, 11 μmol), CuCl (0.4 mg, 4 μmol), K$_2$CO$_3$ (1.4 mg, 11 μmol), and Organotin Compound 7 (0.8 mg, 1.1 μmol) dissolved in NMP (300 μL) was cooled to keep the temperature below −10° C. until [$^{11}$C]CH$_3$I was prepared. [$^{11}$C]CH$_3$I was prepared from [$^{11}$C]CO$_2$ by the conventionally known LiAlH$_4$ method, and in the state where cooling was stopped, [$^{11}$C]CH$_3$I gas was introduced into the reaction solution containing palladium, and rapidly heated to 100° C., the reaction solution was bubbled with nitrogen gas for 2 minutes after 2 minutes. After bubbling, the reaction solution was cooled for 10 seconds, 0.5 M LiOH (600 μL) was added to the mixture, and bubbling with nitrogen at 100° C. for 3 minutes was performed. Then the reaction solution was diluted with a CH$_3$CN/H$_2$O (35:65 v/v, 600 μL) solution containing sodium ascorbate (2.2 mg, 11 μmol), then passed through a fine filter F (F 162, Forte Grow Medical co., Ltd.) filled with quartz glass wool (Tosho co., Ltd.) and separated by HPLC (mobile phase, CH$_3$CN/20 mM sodium phosphate (pH 4.9) 5:95 and 35:65 column, CAPCELL PAK C 18 MG 120 20 (id)×250 mm flow rate 10 ml/min UV detection 280 nm retention time 21 min). From the peak area in radio-HPLC, the HPLC analysis yield was 97±1% (n=3) (see FIG. 6). The fraction containing the desired product was placed in a flask and the organic solvent was removed under reduced pressure. The residue was dissolved in physiological saline (3.0 mL) in which 0.25% polysorbate was dissolved, and a formulation for intravenous administration was prepared. Total synthesis time from completion of irradiation to preparation of injection containing purification by preparative HPLC totaled 47 minutes. After completion of the synthesis, the radioactivity was 1.76±0.42 GBq (n=2), and the specific activity was 95 to 99 GBq/μmol (n=2). The disintegration-corrected yield calculated on the trapped [$^{11}$C]CH$_3$I was 20±1% (n=2). $^{11}$C labeled Compound 2 was confirmed by co-injection of unlabeled Compound 2 on HPLC (mobile phase, CH$_3$CN and 20 mM sodium phosphate=40:60, CAPCELL PAK C 120, 20 (id)×250 mm flow rate 1 ml/min, UV detection 280 nm, retention time 6.1 min). The chemical purity measured at 280 nm wavelength was >92% and the radiochemical purity was >97%. Higher radioactive formulations tended to have lower radiochemical purity.

Figure 5:
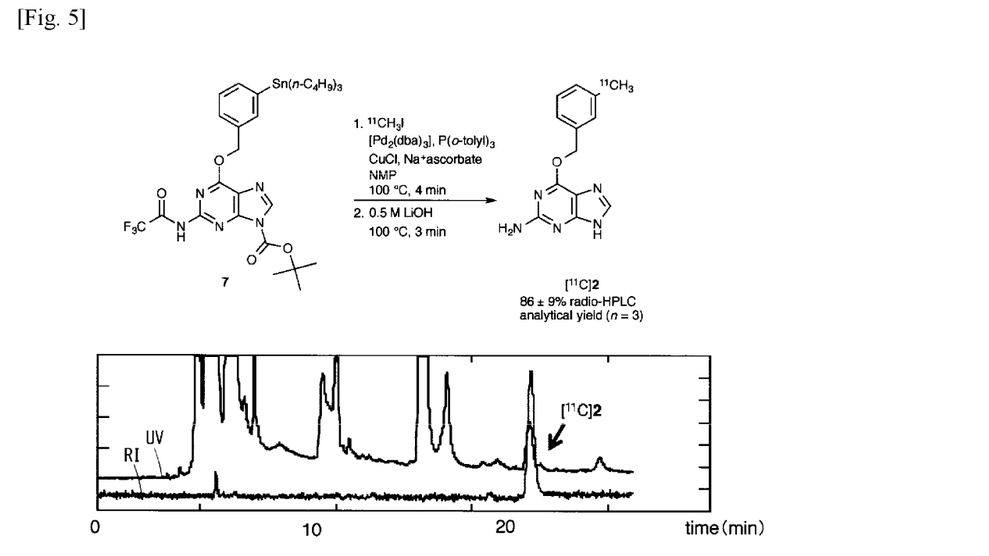
FIG. 5 is a labeling synthesis reaction formula and an HPLC chart in the case where an organotin compound 7 in which the amino group at the 2-position is protected with a trifluoroacetyl group and the amino group at the 9-position is protected with a tert-butoxycarbonyl (BOC) group is methylated by $[^{11}C]$ $CH_3I$ (An added base is sodium ascorbate).

Synthesis of $O^6$-(3-[$^{11}$C] methylbenzyl)guanine ([$^{11}$C](2)) when Sodium Ascorbate is Used as a Base A mixture of [Pd$_2$(dba)$_3$] (1.0 mg, 1.1 μmol), P(o-tolyl)$_3$ (3.4 mg, 11 μmol), CuCl (0.4 mg, 4 μmol), sodium ascorbate (2.2 mg, 11 μmol), and Organotin Compound 7 (0.8 mg, 1.1 μmol) dissolved in NMP (300 μL) was cooled to keep the temperature below −10° C. until [$^{11}$C]CH$_3$I was prepared. [$^{11}$C]CH$_3$I gas was introduced into the reaction solution and rapidly heated to 100° C., then bubbled with nitrogen gas for 2 minutes after 2 minutes. After bubbling, the reaction solution was cooled for 10 seconds, 0.5 M LiOH (600 μL) was added to the mixture, and bubbling with nitrogen at 100° C. for 3 minutes was performed. Then the reaction solution was diluted with a CH$_3$CN/H$_2$O (35:65 v/v, 600 μL) solution containing sodium ascorbate (2.2 mg, 11 μmol), then passed through a fine filter F (F 162, Forte Grow Medical co., Ltd.) filled with quartz glass wool (Tosho co., Ltd.) and separated by HPLC (mobile phase, CH$_3$CN/20 mM sodium phosphate (pH 4.9) 5:95 and 35:65 column, CAPCELL PAK C 18 MG 120 20 (id)×250 mm flow rate 10 ml/min UV detection 280 nm retention time 21 min). From the peak area in radio-HPLC, the HPLC analysis yield was 86±9% (n=3) (see FIG. 5). The fraction containing the desired product was placed in a flask and the organic solvent was removed under reduced pressure. The residue was dissolved in physiological saline (3.0 mL) in which 0.25% polysorbate was dissolved, and a formulation for intravenous administration was prepared. Total synthesis time from completion of irradiation to preparation of injection containing purification by preparative HPLC totaled 48 to 51 minutes. After completion of the synthesis, the radioactivity was 0.92±0.32 GBq (n=3), and the specific activity was 74 to 76 GBq/μmol (n=3). The disintegration-corrected yield calculated on the trapped [$^{11}$C]CH$_3$I was 15±8% (n=3). $^{11}$C labeled Compound 2 was confirmed by co-injection of unlabeled Compound 2 on HPLC (mobile phase, CH$_3$CN and 20 mM sodium phosphate=40:60, CAPCELL PAK C 120, 20 (id)×250 mm flow rate 1 ml/min, UV detection 280 nm, retention time 6.1 min). The chemical purity measured at 280 nm wavelength was >97% and the radiochemical purity was >93%.

In the $^{11}$C-labeled $O^6$-benzylguanine of the above example, a methyl group labeled with $^{11}$C was bonded to the meta position of the benzene ring, but it is also possible to bind a methyl group labeled with $^{11}$C to the ortho position or the para position of the benzene ring by changing the bonding position of the organotin substituent in the organotin compound as a raw material.

<Pharmacokinetics Test Using Rats>

Regarding $O^6$-(3-methylbenzyl) guanine (2) and $O^6$-(4-methylbenzyl) guanine (3) not labeled with $^{11}$C synthesized by the above method (that is, cold), brain permeability was evaluated by the following method.

After intravenous administration (10 mg/kg) of $O^6$-(3-methylbenzyl) guanine (2) or $O^6$-(4-methylbenzyl) guanine (3) to Sprague-Dawley rats, blood and brain tissues were collected after a predetermined time, and analyzed by HPLC. The results are shown in Table 1 and FIGS. 1 to 3.

TABLE 1

Concentration in the brain and brain/plasma ratio after intravenous administration (10 mg/kg) of mMeBG (2) (or pMeBG (3)) to rats

| | Time[a] min | Conc. HPLC[b] μg/mL | | | Brain Weight g | | | Conc. brain[c] μg/mL | | | Conc. Plasma[d] μg/mL | | Brain/Plasma ratio[h] | | |
|---|---|---|---|---|---|---|---|---|---|---|---|---|---|---|---|
| | | | | | mMeBG (2) | | | | | | | | | | |
| Under anaesthesia, fasting | 30 | 0.507 0.568 0.464 | Ave. 0.513 | S.D. 0.052 | 1.860 1.840 1.835 | Ave. 1.845 | S.D. 0.013 | 1.325 1.495 1.223 | Ave. 1.348 | S.D. 0.137 | 4.450 4.450 4.450 | e | 0.298 0.336 0.275 | Ave. 0.303 | S.D. 0.031 |

TABLE 1-continued

Concentration in the brain and brain/plasma ratio after intravenous administration (10 mg/kg) of mMeBG (2) (or pMeBG (3)) to rats

| | Time$^a$ min | Conc. HPLC$^b$ μg/mL | | | Brain Weight g | | | Conc. brain$^c$ μg/mL | | | Conc. Plasma$^d$ μg/mL | | Brain/Plasma ratio$^h$ | | |
|---|---|---|---|---|---|---|---|---|---|---|---|---|---|---|---|
| Under nonanaesthesia, fasting | 30 | 0.536 0.635 0.474 0.481 0.454 0.555 | Ave. 0.523 | S.D. 0.067 | 1.861 1.909 1.677 1.785 1.854 1.888 | Ave. 1.829 | S.D. 0.086 | 1.400 1.634 1.323 1.291 1.188 1.436 | Ave. 1.379 | S.D. 0.152 | 5.192 5.192 5.192 5.192 5.192 5.192 | f | 0.270 0.315 0.255 0.249 0.229 0.277 | Ave. 0.265 | S.D. 0.029 |
| Under anaesthesia, nonfasting | 30 | 0.784 0.684 0.522 | Ave. 0.663 | S.D. 0.132 | 2.121 1.885 1.970 | Ave. 1.992 | S.D. 0.120 | 1.893 1.772 1.318 | Ave. 1.661 | S.D. 0.303 | 4.450 4.450 4.450 | e | 0.425 0.398 0.296 | Ave. 0.373 | S.D. 0.068 |
| | | | | | | pMeBG (3) | | | | | | | | | |
| Under anaesthesia, fasting | 44 32 | 0.118 0.231 | | | 2.020 1.900 | | | 0.470 0.959 | | | 2.481 2.481 | g | 0.189 0.386 | | |

Abbreviations:
average (Ave.),
standard deviation (S.D.)
$^a$Time is blood removal time after i.v. administration.
$^b$Conc. HPLC is concentration (micro g/mL) of compound in brain homogenate determined by HPLC analysis.
$^c$Conc. brain (micro g/mL) was calculated from [conc. HPLC (micro g/mL)] × [volume of brain homogenate (mL)]/[brain weight (g)]. Here, the specific gravity of brain is set to 1, and micro g/g is converted to micro g/mL.
$^d$Plasma sample was collected from another rat different from brain sample.
$^e$Average (n = 5) of the plasma concentration 30 min after i.v. administration (10 mg/kg) of 2 in rat under anaesthesia and fasting.
$^f$Average (n = 3) of the plasma concentration 30 min after i.v. administration (10 mg/kg) of 2 in rat under nonanaesthesia and fasting.
$^g$Average (n = 3) of the plasma concentration 30 min after i.v. administration (10 mg/kg) of 3 in rat under anaesthesia and fasting.
$^h$Brain/Plasma ratio was calculated from [conc. brain (micro g/mL)]/[conc. plasma (micro g/mL)].

The results of collecting samples of brain tissue and blood 30 minutes after administration of Compound (2) (or Compound (3)) are shown in Table 1. The amount of the compound in the brain is calculated from the brain weight and the brain concentration in Table 1, from the ratio of the amount of the compound in the brain to the dose, the concentration of the compound in the brain of the compound (2) and the compound (3) were calculated to be 0.1% based on the total dose. In addition, the ratio to the concentration in the plasma was 0.3. From the above results, it was evaluated that the compound (2) and the compound (3) are substances having blood-brain barrier permeability.

Figure 7:
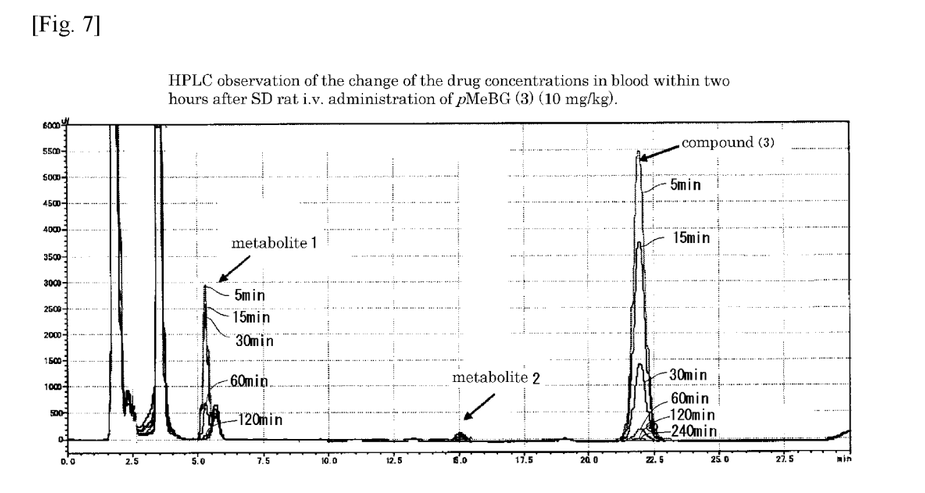
FIG. 7 is an HPLC chart showing changes in blood concentration after administration of pMeBG (3) to SD rats.
Figure 8:
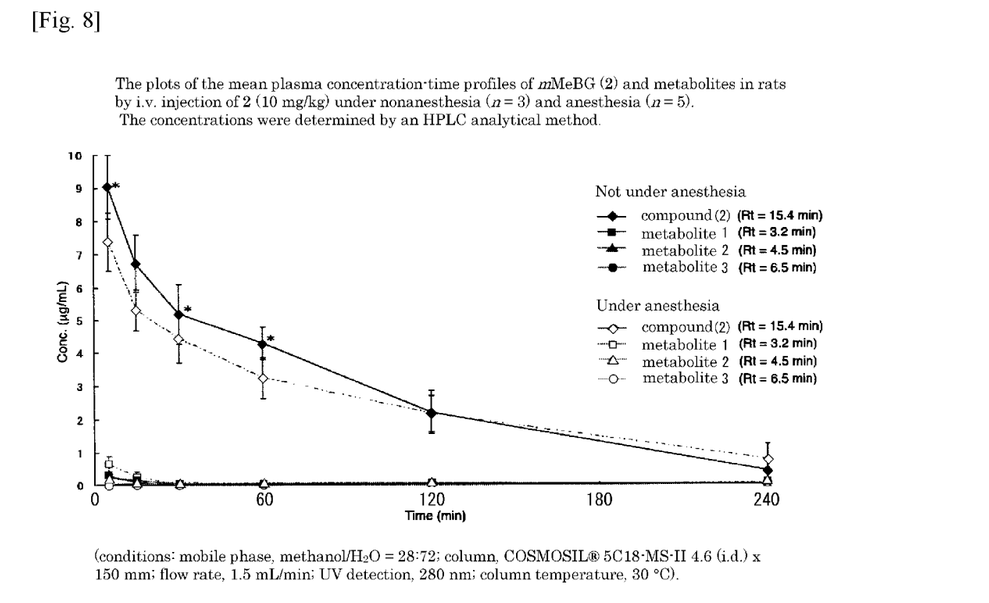
FIG. 8 is a graph showing the time course of the average plasma concentration of mMeBG (2) and its metabolites after administration of Compound 2 to rats.
Figure 9:
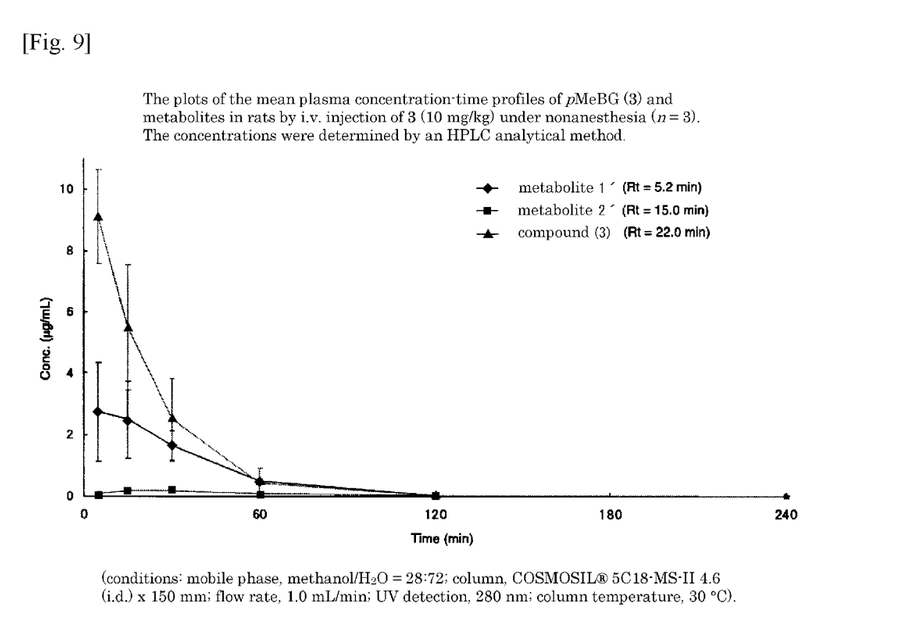
FIG. 9 is a graph showing the time course of the mean plasma concentration of pMeBG (3) and its metabolites after administration of Compound 3 to rats.

Compound (2) and compound (3) stably exist in the plasma, but as shown in FIG. 7 and FIG. 9, compound (3) is quickly metabolized to unknown, more polar compounds within 240 minutes after intravenous administration to rats, as shown in FIG. 8, it was found that the compound (2) was more stable than the compound (3) and was present for a long time.

It was clarified by the above body pharmacokinetics test that $O^6$-(3-methylbenzyl)guanine (2) and $O^6$-(4-methylbenzyl)guanine (3) are substances with blood-brain barrier permeability and are accumulated in the brain. Since these compounds have the property of binding to MGMT in the brain, $O^6$-benzylguanine of the present invention labeled with $^{11}C$ of these compounds is useful as a PET probe, and it became possible to image MGMT in the brain.

The present invention is not limited to the embodiments and examples of the invention. Various modifications are also included in the present invention as long as those skilled in the art can easily devise without departing from the scope of the claims.

INDUSTRIAL APPLICABILITY

Since the present invention can be used for imaging of MGMT using a PET apparatus, it can be used for research on in vivo dynamics of MGMT, cancer diagnosis in brain cancer, and the like.

The invention claimed is:

1. A PET probe comprising a $^{11}C$-labeled $O^6$-benzylguanine represented by the following chemical formula (a):

(a)

which has a chemical purity of 99% or more and a radiochemical purity is 99% or more.

2. The PET probe comprising a $^{11}C$-labeled $O^6$-benzylguanine according to claim 1,
wherein a methyl group labeled with $^{11}C$ is bonded to a meta position of a benzene ring.

3. A method for imaging an MGMT, comprising:
administering the PET probe of claim 1 to a living body; and
capturing a PET image of said probe in said living body.

4. A method for producing the PET probe comprising a $^{11}C$-labeled $O^6$-benzylguanine according to claim 1, comprising:
a coupling step of cross-coupling a methyl iodide labeled with $^{11}C$ and the following organotin compound (b) (R1 represents an alkyl group, and $R^2$ and $R^3$ represent a leaving group which can be eliminated with a base)

in the presence of a palladium complex, a phosphine ligand, and cuprous halide in an aprotic lactam, and a desorption step of desorbing the leaving groups $R^2$ and $R^3$ of the coupling product obtained by the coupling step with a base:

(b)

5. The method for producing the $^{11}$C-labeled $O^6$-benzylguanine according to claim 4, wherein $SnR^1_3$ is bonded to a meta position of a benzene ring.

6. The method for producing the $^{11}$C-labeled $O^6$-benzylguanine according to either claim 4 or claim 5, wherein $R^2$ is a trifluoroacetyl group and $R^3$ is a tert-butoxycarbonyl group.

7. The method for producing the $^{11}$C-labeled $O^6$-benzylguanine according to claim 4, wherein the aprotic lactam is N-alkyl-2-pyrrolidinone.

8. The method for producing the $^{11}$C-labeled $O^6$-benzylguanine according to claim 4, wherein in the coupling step, at least one of a carbonate salt, a fluoride of an alkali metal and an alkali metal salt of ascorbic acid is added.

9. The method of claim 3, wherein the PET image is of the brain of the living body.

* * * * *